United States Patent [19]

Humphrey

[11] Patent Number: 5,103,223
[45] Date of Patent: Apr. 7, 1992

[54] STREET CROSSING SIGNAL

[76] Inventor: Jerry J. Humphrey, 4961 Van Buren, Yorba Linda, Calif. 92686

[21] Appl. No.: 471,086

[22] Filed: Jan. 26, 1990

[51] Int. Cl.⁵ .......................................... G08G 1/095
[52] U.S. Cl. .................................... 340/944; 340/407
[58] Field of Search ........... 340/944, 407, 925, 825.19; 40/612, 613; 128/33, 41; 434/112

[56] References Cited

U.S. PATENT DOCUMENTS

| 494,337 | 3/1893 | King ................................. 340/407 |
| 2,461,448 | 2/1949 | Smith ............................. 340/944 X |
| 2,754,505 | 7/1956 | Kenyon ............................ 340/407 |
| 4,139,742 | 2/1979 | Walker ........................... 340/407 X |
| 4,590,474 | 5/1986 | Patterson . |
| 4,635,287 | 1/1987 | Hirano ............................. 128/33 X |
| 4,851,836 | 7/1989 | Wilkinson et al. . |

FOREIGN PATENT DOCUMENTS 2375672 7/1978 France .
8200709 9/1983 Netherlands .

OTHER PUBLICATIONS

Audio Tactile Pedestrian Detector, Aldridge Traffic Systems Brochure.
Traffic Signals for the Blind, The American City, p. 50, May 1969.

Primary Examiner—Jin F. Ng
Assistant Examiner—Brian R. Tumm
Attorney, Agent, or Firm—Knobbe, Martens, Olson & Bear

[57] ABSTRACT

A street crossing signal for the visually impaired is disclosed. The signal acts cooperatively with the traffic signals to provide a tactile indication of the proper time to cross a street. A vibrator unit is retained relative to a panel having an indicator window therethrough which allows contact with the vibrator unit. The vibrator unit is retained relative to the panel and frame so that vibration of the unit is not transferred to the panel or the frame.

15 Claims, 4 Drawing Sheets

STREET CROSSING SIGNAL

FIELD OF THE INVENTION

The present invention relates to pedestrian street crossing signs, and, in particular, to a street crossing signal for enhancing the knowledge of the characteristics of an intersection so as to assist the visually impaired.

BACKGROUND OF THE INVENTION

The most common type of street crossing sign for assisting the visually impaired employs an audible signal to indicate when it is safe to cross the street. While the sound employed by the audible signal may vary, the typical sound is a simulated bird sound, with a different bird sound representing a different direction in which to cross. The audible systems are typically associated with existing street crossing signs and are designed so that the tone emanates from the area of the walk indicator when the walk indicator is activated.

However, in order to be heard over the noise of the traffic at an intersection, the sounds must be of a substantive volume. The audible signals typically employ feedback systems so that the emitted sound is a predetermined level above the ambient noise level. This increased volume is extremely distracting to drivers, and also makes it difficult to hear sirens from emergency vehicles. In addition, the audible signals can be bothersome to local residents and businesses proximal to the signal.

The audible signals have another disadvantage in that these signals call attention to the users of the signal and identify them as visually impaired. As many of the visually impaired are highly self sufficient, they do not wish to draw attention to themselves and desire a discrete street crossing system which can be used without attracting undue attention.

In addition, the audible signal crossing aids do not provide additional information which is helpful to the pedestrian, such as the distance between curbs and/or the number of lanes to be crossed, the name of the streets at the particular crossing, or the presence of hazards in the intersection, such as construction barriers or islands.

The prior attempts to provide a suitable street crossing aid for the visually impaired have included the U.S. Pat. No. 4,570,474 issued to Patterson, entitled "Street Crossing Signal Device for Blind Persons." The Patterson device comprises a pair of rigid hand rails secured to a post at the corner of the intersection, such that each hand rail has a portion oriented in the direction of a corresponding crosswalk. The device further includes a vibrator means disposed within each hand rail, which vibrates when the traffic lights permit crossing in the direction of the rail.

However, as each hand rail extends from the post, the rail represents a substantial obstruction to the flow of pedestrian traffic. Pedestrians are forced to navigate around each hand rail in order to pass the post. Further, the addition of hand rails to existing sign posts represents a time-consuming, labor-intensive, and therefore expensive process.

Therefore, a need exists of a street crossing signal for the visually impaired which is readily adapted to existing crossing technology and does not draw undue attention to those who use the signal. The need also exists for a street-crossing signal for the visually impaired which provides additional information such as the name of the street to be crossed, the direction to walk, the distance between curbs and a silent indication of when it is safe to cross, i.e., when the walk interval occurs.

SUMMARY OF THE INVENTION

The present invention provides a street crossing signal for use by the visually impaired, which is readily compatible with existing crossing signal configurations. The disclosed signal also provides the user with the name of the street to be crossed, the distance between the curbs, the direction to walk, and when it is safe to walk.

The present invention cooperates with the existing traffic signals to provide a silent, localized vibrating surface during the walk interval; that is, when it is safest to cross the street. The preferred embodiment of the disclosed signal includes an adaptor mounted to the existing frame and sign post. Preferably, the frame and the post form a chamber or cavity which the adaptor substantially closes. The adaptor is engaged with the frame so as to substantially close the chamber and enclose the working components within the chamber. Preferably, the adaptor includes a panel having an indicator window or aperture, a vibrator unit and isolation system retaining the vibrator unit relative to the panel. Preferably, the vibrator unit is affixed to the panel by the isolation system so that the vibrator unit is proximal to the window in the panel of the adaptor. The isolation system permits the vibrator unit to oscillate or vibrate without transferring any substantial vibrations to the panel, the frame or the post.

The vibrator unit includes an armature assembly and coil, wherein the armature assembly vibrates when an electrical current is passed through the coil. More specifically, the vibrator includes a coil having a plurality of electrically conductive loops which are fixed with respect to an undercarriage. The armature assembly includes two magnets positioned such that the coil is disposed between the magnets without contacting the magnets. The undercarriage includes a suspension system for retaining the armature assembly relative to the coil and the undercarriage. A lid engages the undercarriage to enclose the suspended armature assembly such that the lid and undercarriage form a box. The vibrator unit is mounted to the panel of the adaptor proximal to an aperture therethrough, using an isolation system which prevents movement of the armature assembly from being dispersed throughout the panel and frame.

DETAILED DESCRIPTION OF THE DRAWINGS

Figure 2:
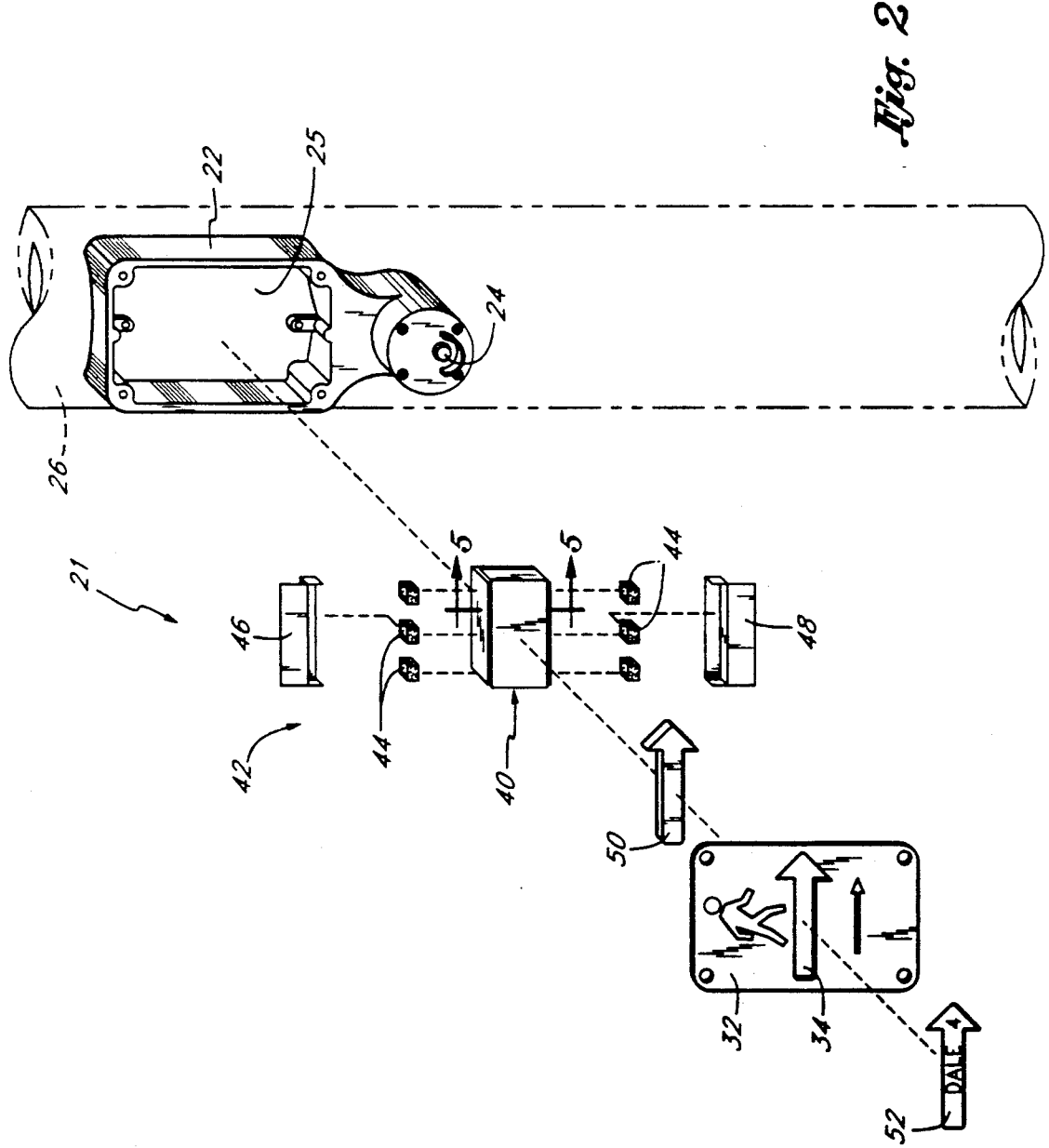
FIG. 2 is an exploded perspective of the present invention.
Figure 5:
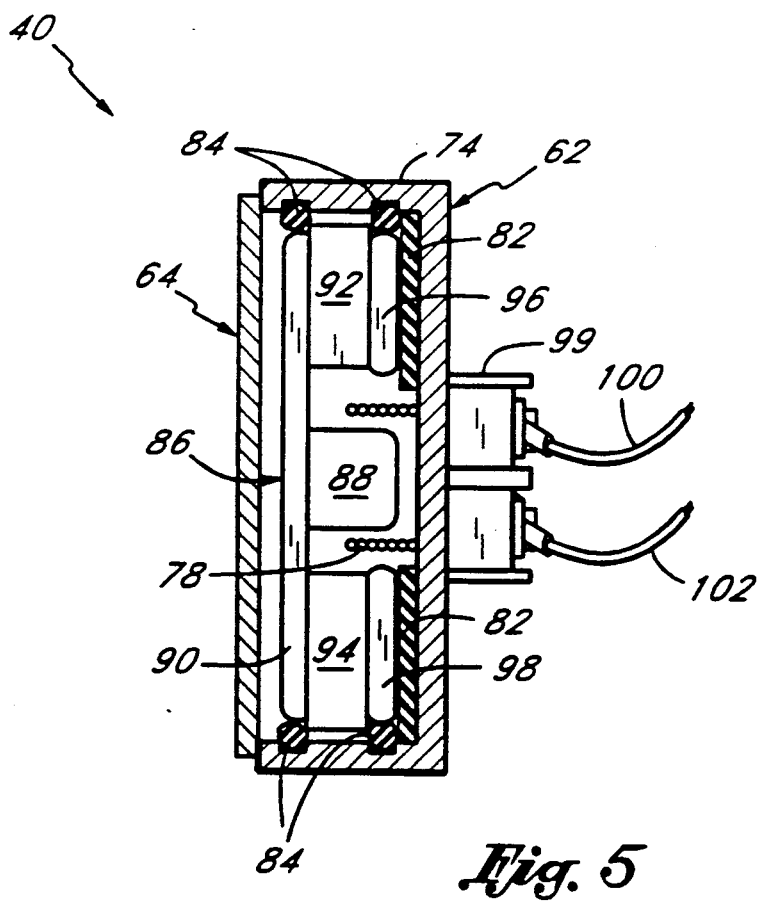

FIG. 5 a cross-section of the vibrator unit taken along lines 5—5 of FIG. 2.

DETAILED DESCRIPTION OF THE INVENTION

Figure 1:
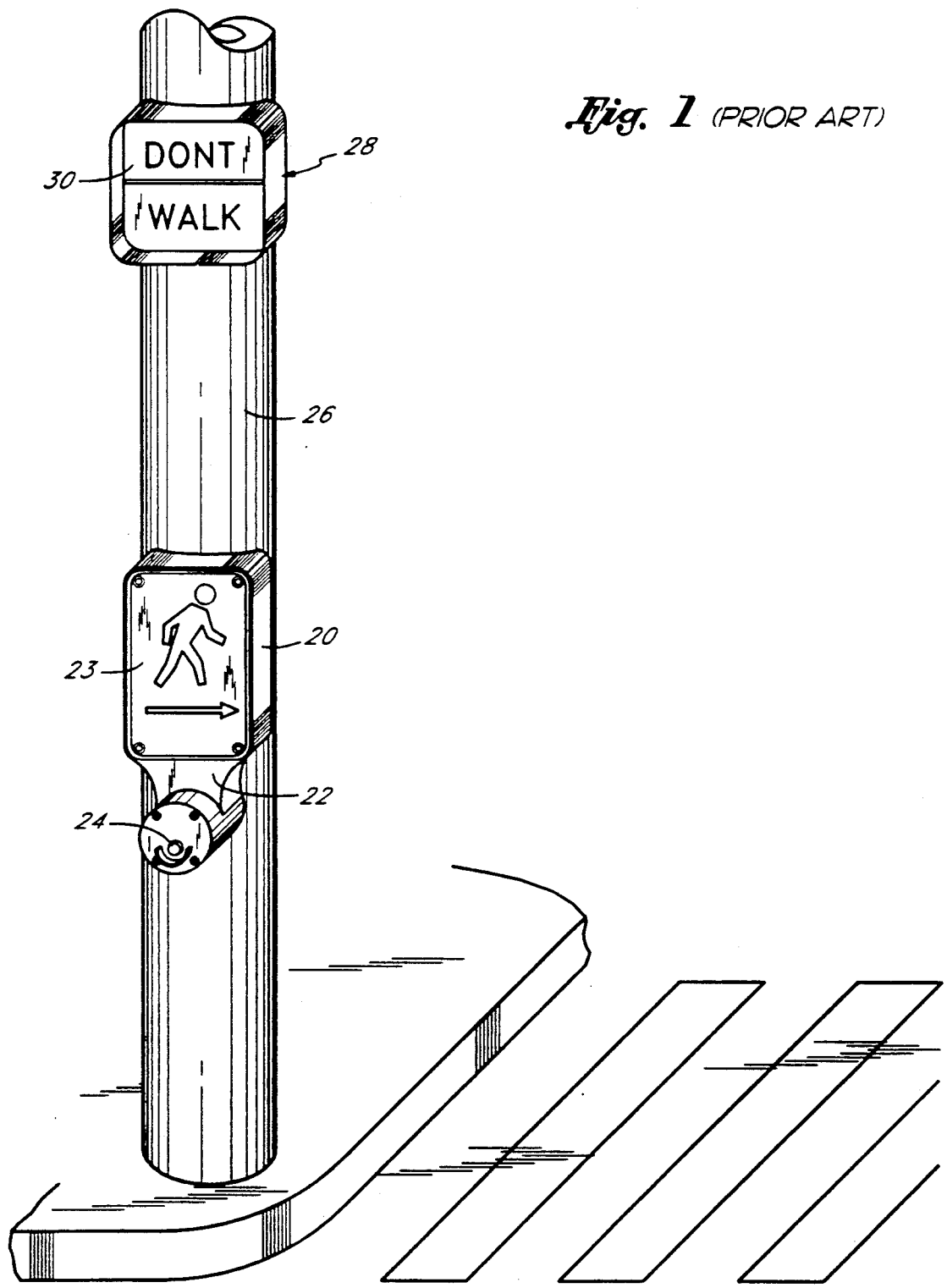
FIG. 1 is a perspective view of an existing prior art signal.

Referring to FIG. 1, the present invention is designed to be installed as an adaptor in place of the plate 23 on a pedestrian control box 20. The box 20 includes a frame 22, typically having a call button 24 and the panel 23. The call button 24 allows a pedestrian to interface with the traffic signals so as to cross the street. Alternatively, the frame 22 may be constructed without a call button 24. The frame 22 is mounted on a signal post 26 which is typically located at each corner of an intersection. An indicator sign 28 is also mounted on or near the signal post 26 above the sign 20 and is provided with a display 30 which is usually in the form of letters or international symbols and indicates the walk interval to a pedestrian; that is, when it is safe to "walk," i.e., to proceed to cross the street.

As shown in FIG. 2, the adaptor 21 includes a rectangular sign panel 32 mounted to the front of the frame 22. As shown in FIG. 2, preferably the frame 22 and post 26 form a cavity or chamber 25 into which operating components of the adaptor 21 may be retained. If the chamber is too small, a spacer or gasket (not shown) may be disposed between the panel 32 and the frame 22 so as to increase the volume of the chamber 25. Typically, the panel 32 is mounted to the frame 22 by screws or bolts. The panel 32 is preferably porcelain plated as required by industry specifications. However, other exterior coatings known in the industry ma be employed. The panel 32 includes an indicator window 34 formed in the center of the panel 32. Although the disclosed window 34 is in the shape of an arrow, other configurations such as checks or angles may be employed. Alternatively, the indicator window 34 may comprise a recess from an edge of the panel 32. The window 34 is designed so that a portion of a vibrator unit 40 may be exposed through the panel 32. Preferably, the indicator window 34 is located in the center region of the panel 32. This center orientation of the window 34 provides space for the visual information which is provided on the prior art sign 23, as shown in FIG. 1, to be displayed in connection with the present invention. In addition, the center location of the window 34 provides the most room for clearance behind the panel 32. However, the window 34 may be located anywhere in the panel 32 so long as the vibratory unit 40 is exposed through the window 34.

The panel 32 may be formed of 0.1 inch thick (#10 AWG) low carbon cold rolled steel. Although prior art plates 23 have a thickness of approximately 0.04 inches (#18 AWG), the thicker steel is preferable to ensure rigidity of the sign and to prevent any undesired transfer of vibrations. As shown in FIG. 2, when the panel 32 is mounted to the frame 22, the chamber 25 formed by the post 26 and frame 22 is substantially closed. Alternatively, the frame 22 may include a back wall (not shown) so as to substantially form the chamber 25 independent of the post 26. In addition, as the post 26 may be substantially cylindrical or rectangular in cross section, the chamber may be of a variety of configurations.

Referring to FIG. 2, an isolation system 42 retains the vibrator unit 40 within the chamber 25 and relative to the panel 32 so that a portion of the vibrator unit 40 is exposed through the indicator window 34.

A spacer 50 is attached to the vibrator unit 40 and protrudes through the window 34. The spacer 50 is preferably an insulative material such as LEXAN and is bonded to the vibrator 40 by a LEXAN-anodized steel compatible adhesive tape, such as VHB-type 4945 as manufactured by Minnesota Manufacturing & Mining, but may also be fastened using screws or bolts An indicator 52 is attached to the spacer 50 such that the indicator 52 projects through the window 34 from the plane of the panel 32. The indicator 52 may be formed of nickel-plated steel. Preferably, the indicator 52 is sized to be slidably received through the window 34, and in the preferred embodiment, the indicator 52 is an arrow, as shown in FIG. 2. Preferably the indicator 52 includes raised letters and/or numbers such as "DALE 4" to indicate the name of the street to be crossed, Dale, and the number of lanes to be crossed 4. The letters are preferably in the Helvetica or Futura Demi style, with a one-half inch minimum height and are raised no less than 0.03 inches from the surface of the indicator 52.

Referring to FIG. 2, the isolation system 42 retains the vibrator unit 40 relative to the panel 32. The isolation system 42 includes a plurality of isolation pads 44 made of a silicon rubber foam. A preferable composite foam rubber is AMS-3195, as defined by standard industry specifications. The vibrator unit 40 is attached to the pads 44 with a silicon rubber adhesive, such as RTV-732 or equivalent, manufactured by Dow Corning. Preferably, the isolation pads 44 are attached to the sides of the vibrator unit 40 and the panel 32. The shields 46 and 48 cover the isolation pads 44 and are secured to the panel 32 so as to protect the pads 44 from mishandling during shipping and installation. The inherent resilient properties of the isolation pads 44 prohibit the vibrational movement produced by the vibrator unit 40 from being transferred to the panel 32. The vibrator 40 must be mounted so that it may vibrate relative to the panel 32, without contacting the panel 32. In addition, as the signal will be installed vertically on a post, the gravitational forces must be accommodated. In the preferred embodiment, three isolation pads 44 are equidistantly placed along each of the major sides of the vibrator unit 40 so as to secure the vibrator unit 40 approximately $\frac{1}{8}$" from the panel 32. The vibrational forces of the vibrator unit 40 are transmitted through the spacer 50 to the indicator 52 which is mounted to the vibrator 40 and protrudes through the window 34 in the sign panel 32. In this manner, the vibrational forces are not distributed throughout the frame 22 and are not dispersed to the point where they are unidentifiable by the user.

Figure 3:
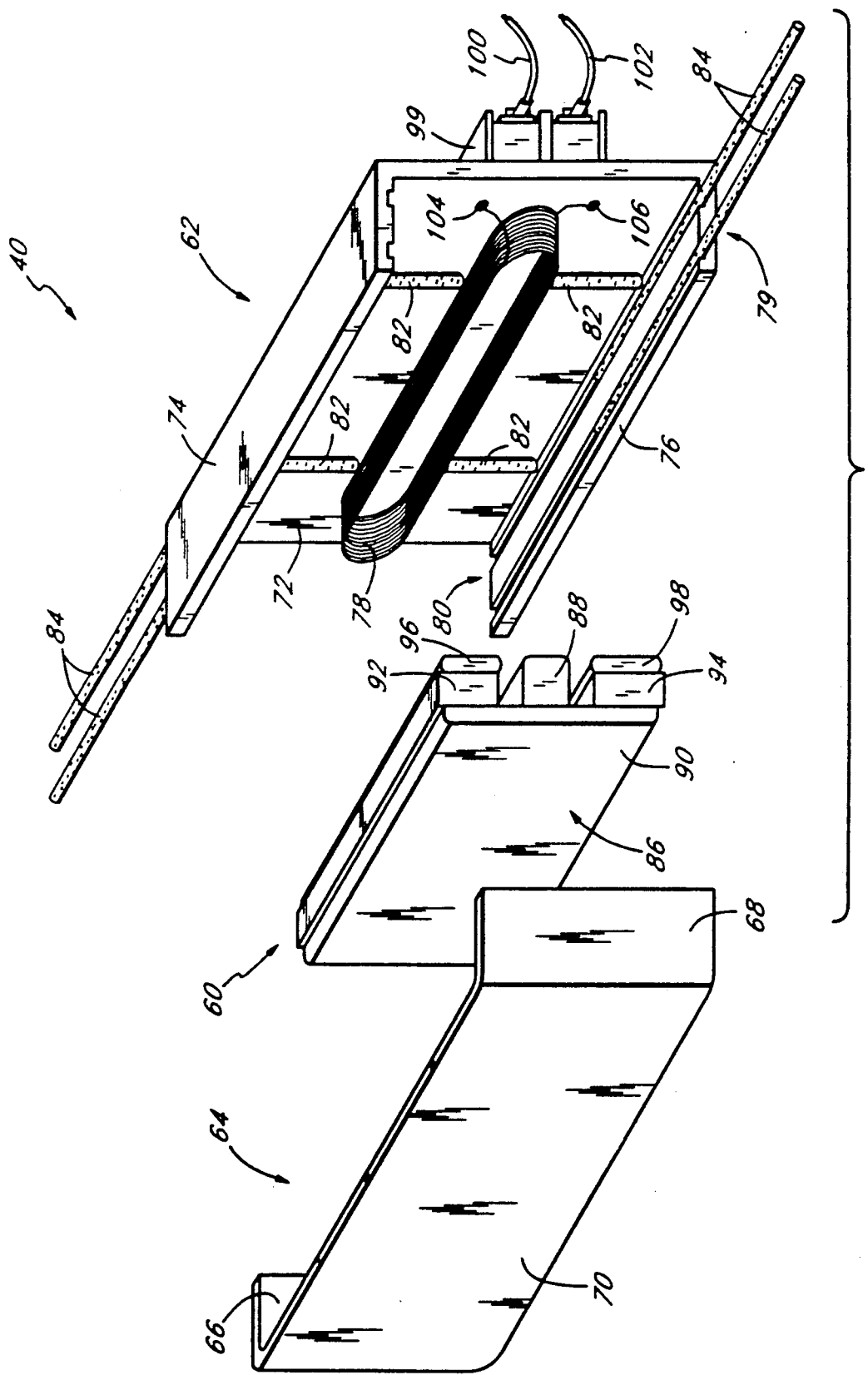
FIG. 3 is an exploded perspective of the vibrator unit of the present invention.

Referring to FIG. 3, the vibrator unit 40 is shown in more detail. The vibrator 40 is a low voltage, compact unit for providing the necessary oscillatory motion. The vibrator unit 40 includes a U-shaped undercarriage 62 and a corresponding U-shaped lid 64 which cooperatively engage to form a box. Preferably, the undercarriage 62 and lid 64 are formed of anodized aluminum to provide a light weight material, which is corrosion-resistant and readily dissipates heat.

As shown in FIG. 3, the lid 64 comprises two end walls 66 and 68 formed integrally with a front wall 70. The undercarriage 62 comprises a back wall 72, a top wall 74, and a bottom wall 76 such that the sides of the undercarriage 62 are open. The undercarriage 62 further includes four longitudinal grooves 80 which extend along the length of the inside of the top and bottom walls 74 and 76. The grooves 80 may be conveniently formed by milling or other methods well known in the art. A plurality of translation pads 82 are fixed to the inside back wall 72. The translation pads are formed of AMS-3195 foam silicon rubber, as defined by industry specifications, and provide for the transmission of the vibratory action, as described infra, to the undercarriage 62. A suspension assembly 79 includes four elongated suspension pads 84 which are retained within the grooves 80. The pads 84 are formed of AMS-3195 foam silicon rubber as described supra and can be retained with the grooves 80 by a friction fit or an adhesive, such as RTV-732, manufactured by Dow Corning or an equivalent.

A cylindrical coil 78 having a plurality of turns is attached to the inside back wall 72 of the undercarriage 62 proximal to the translation pads 82. Preferably, the coil is a high temperature varnish coated copper wire. The coil 78 has approximately thirty loops.

Referring to FIGS. 3 and 5, an armature assembly 60 is contained within the box formed by the U-shaped undercarriage 62 and the corresponding U-shaped lid 64. The armature assembly 60 includes a T-shaped base 86 having a center beam 88 and orthogonal cross beam 90. Although the base 86 is disclosed as two separate pieces, the base 86 may be conveniently formed of a single piece. The base 86 is preferably formed of nickel plated cold rolled steel. Two bar magnets 92 and 94 are disposed on either side of the center beam 88 and are fixedly attached, by glue, epoxy, or by screws and bolts, to the underside of the cross beam 90. The magnets 92, 94 are formed of a ceramic magnet. Two ballast members 96, 98 are fixedly attached to the magnets 92, 94 opposite and parallel to the cross beam 90. The ballast members 96, 98 are also formed of nickel plated cold rolled steel. The magnets 92, 94 are affixed to the cross beam 90 and ballast members 96, 98 by an epoxy, such as HYS-9340 as manufactured by Hysol or an equivalent. A pair of transformer leads 100 and 102 are attached to a two place terminal strip 99 on the outside of the back wall 72 of the undercarriage 62 and are connected at two connection points 104 and 106 to the coil 78.

As shown in FIG. 5, when assembled, the armature assembly 60 is positioned such that the coil 78 surrounds the center beam 88 and is located within the channels formed between the magnets 92, 94 and the center beam 88. The ballast members 96, 98 of the armature assembly 60 rest on the translation pads 82 and contact the suspension pads 84. In this position, the armature assembly 60 is retained by a frictional fit between the suspension pads 84 and the magnets 92, 94 and is thus retained relative to the coil 78. The armature assembly 60 is thereby trapped in place by the pads 82, 84. As the lid 64 is engaged with the undercarriage 62, the armature assembly 60 cannot escape its position, yet the pads 82, 84 permit the necessary freedom allowing the armature assembly 60 to move relative to the coil 78. The lid 64 covers the assembly 60 with the end walls 66 and 68 of the lid 64 enclosing the open sides of the undercarriage 62 such that, when assembled, the lid 64 and undercarriage 62 define a rectangular box which contains the vibrator unit 40. Referring to FIG. 5, as the armature assembly 60 is retained by the suspension assembly 79, the armature assembly does not contact the lid 64 as it engages the undercarriage 62. Preferably, the lid 64 and undercarriage 62 are formed of hard anodized aluminum and sealed together with epoxy, thus completely sealing the vibrator assembly 40 from particulates, water, and other contaminants. A preferred epoxy is a high strength, high temperature epoxy, such as HYS-9340, as described supra. In this manner, the box is corrosion resistant and is also able to dissipate the minimal heat generated by the vibrator unit 40.

Figure 4:
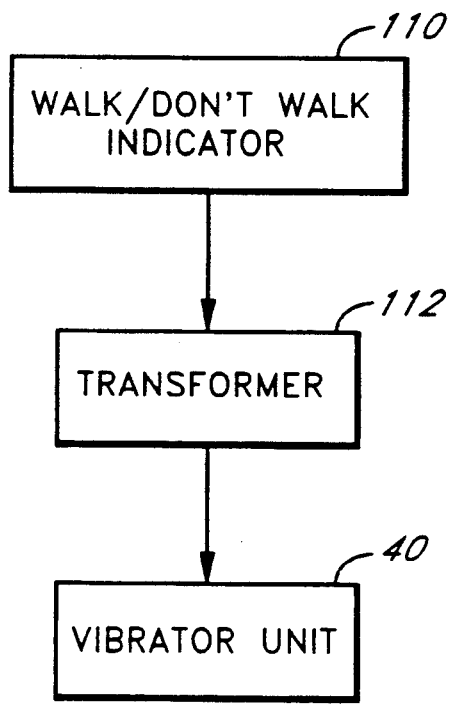
FIG. 4 is a schematic diagram of the electric interconnection of the present invention.

Referring to FIG. 4, power is supplied to the coil 78 from the power source which activates the walk indicator 110. A transformer 112 is required to step down the voltage, typically 120 volts AC, to comply with State and Federal specifications which require that the voltage at the call button not exceed 24 volts AC or DC. The operating voltage required by the vibrator 40 is approximately 5 volts, which requires a transformer 112 with a step-down ratio of approximately 24:1. Once the voltage has been stepped down, it can be supplied to the vibrator 40 via the transformer leads 100 and 102. Preferably, the wires from the transformer 112 to the vibrator unit 40 are stranded and have a size between #19 AWG to #24 AWG. The standard wire is preferred over solid wire because of the higher resistance to failure upon repeated flexing. The wires exit the post 26 at a small hole (not shown), typically 0.25 inches in diameter, which may be drilled into the post.

As shown in FIG. 3, the transformer leads 100 and 102 are connected to the coil 78 at a terminal strip 99 such that when voltage is supplied to the coil 78, a current is induced in the coil 78 which affects the magnetic field produced by the two magnets 92 and 94. The changing magnetic field produces the forces which move the armature assembly 60 within the box at the standard line frequency, which by convention is 60 Hertz in the United States. The vibrational movement experienced by the armature assembly 60 is transferred to the undercarriage 62 and lid 64 via the translation pads 82 mounted on the inside back wall 72 of the undercarriage 62. The thrust voltage and current generate approximately 30 watts to produce a throw of approximately 0.062 inches. If the throw is too large, the tactile sensation is discomforting and is therefore undesirable. Alternatively, if the throw is too small, the vibration is not sufficiently detectable. The translation pads 82 are in contact with the ballasts 96, 98 and thus are in contact with the magnets 92, 94 attached to the ballasts 96 and 98. In this manner, when the armature assembly 60 vibrates as described above, movement is transferred from the assembly 60 to the undercarriage 62 and the lid 64.

Operation

As the frame 22 includes the standard call button 24, the pedestrian initially locates the call button 24 without requiring any guidance or assistance. As the indicator 52, in the shape of an arrow in of the preferred embodiment, protrudes from and is centered on panel 32, directly above the push button 24, the pedestrian is readily able to locate the indicator 52. Upon locating the indicator 52, the pedestrian may "read" the street name to be crossed on the indicator 52, thereby making the decision whether to employ the crossing button 24. Further, upon locating the indicator 52, the pedestrian is able to determine which way the indicator 52 was pointing, thereby indicating the direction in which to walk. Further, as the street name is taken from the indicator 52, the number of lanes between the curbs is also determined with the same finger movements. Upon knowing the street name, the number of lanes and the direction in which to cross, the pedestrian may then employ the call button 24, and upon the silent vibration of the indicator 52 during the walk interval, proceed across the street, knowing the number of lanes to be crossed.

When the lights are such that it is safe to cross, the standard walk indicator 110 is activated. As the vibrator unit 40 is in electrical communication with this circuit, the vibrator unit 40 concurrently vibrates, thereby causing the indicator 52 to vibrate. As the vibratory motion is substantially silent, there is no undue attention drawn to the user. In addition, as only the indicator 52 vibrates, the frame 22 and panel 32 remain substantially stationary. When it becomes unsafe to cross the street, the walk indicator 110 shuts off, and thus no power is supplied to the vibrator unit 40. The vibration ceases and the indicator 52 becomes stationary, thereby indicating to the user that it is not safe to cross.

Although the present invention has been described in terms of particular embodiments, it is not limited to these embodiments. Alternative embodiments and modifications which would be encompassed by the invention may be made by those skilled in the art, particularly in light of the foregoing teachings. Alternative embodiments, modifications or equivalents may be included within the spirit and scope of the invention as defined by the claims.

What is claimed is:

1. A street crossing signal for providing tactile information during a walk interval, comprising:
  (a) a post;
  (b) a frame mounted to the side of the post, the frame and the post forming a chamber;
  (c) a panel affixed relative to the frame, the panel having an indicator window therethrough and sized to engage the frame so as to substantially enclose the chamber; and
  (d) a vibrator unit for selectively vibrating during the walk interval affixed to the panel proximal to the indicator window so that the indicator window exposes a portion of the vibrator unit, the vibrator unit extending from the panel into the chamber, the vibrator unit being totally supported by the panel and not by the frame except through the panel.

2. The street crossing signal of claim 1, wherein the frame extends outwardly from the post and the frame is formed by at least one projecting member.

3. The street crossing signal of claim 1, further comprising an isolation system mounting the vibrator unit to the panel so that upon actuation of the vibrator unit the panel and the frame remain substantially stationary, the isolation system comprises a plurality of isolation pads positioned to isolate the vibrator unit from the panel and mounting structure.

4. The street crossing signal of claim 1, further comprising an indicator sized to be received through the indicator window in the panel and affixed to the vibrator unit, so that upon vibration of the vibrator unit, the indicator vibrates without contacting the panel.

5. The street crossing signal of claim 1, wherein an assembly comprising the panel and vibrator unit is adapted to mount and dismount from the frame while the frame is affixed to the post.

6. A street crossing signal adapted to be partially retained within a chamber formed by a side wall frame on a post, such that the signal provides tactile information corresponding to a walk interval, comprising:
  (1) a substantially rigid flat panel sized to engage the frame so as to form a front wall of the chamber, said panel includes an indicator window such that a portion of the chamber is exposed; and
  (2) a vibrator unit for providing tactile information corresponding to the walk interval, wherein said vibrator unit includes;
  (a) an undercarriage sized to be retained within the frame;
  (b) a coil affixed to the undercarriage, the coil having a plurality of electrical conductive loops and at least one electrical contact extending from the undercarriage;
  (c) an armature assembly including a pair of parallel magnets spaced to receive the coil;
  (d) a suspension assembly for retaining the armature assembly relative to the coil; and
  (e) a lid for closing the armature assembly, retained by the suspension assembly, such that the lid is sized to engage the undercarriage;

and the vibrator unit is affixed directly to the panel so that a portion of the vibrator unit is exposed to the indicator window and said panel is adapted to be coupled to the frame such that the vibrator unit is totally supported only by the panel, and is not supported by the frame except by way of the panel.

7. The street crossing signal of claim 6, wherein the suspension assembly retains the armature assembly relative to the coil by a friction engagement between the undercarriage and the armature assembly.

8. A street crossing signal for providing tactile information, adapted to be received within a chamber formed by a side wall frame affixed to a post, comprising:
  (a) a panel affixed to an open front of the frame so as to form a front wall of said chamber, said panel including an indicator window therethrough; and
  (b) a vibrator unit affixed to and totally supported by the panel proximal to the indicator window, said unit being sized to be freely received within the chamber without being supported by the frame except through the panel, the vibrator unit including an armature assembly and a coil wherein the armature assembly is moved relative to the coil upon the passage of an electric current through the coil.

9. The street crossing signal of claim 8, further comprising an indicator configured to be received within the indicator window of the panel, wherein the indicator is mechanically linked to the vibrator unit so that upon vibration of the vibrator unit, the indicator vibrates relative to the panel.

10. The street crossing signal of claim 8, wherein the indicator window is in the shape of an arrow.

11. The street crossing signal of claim 8, wherein panel and the vibrator unit are readily compatible with the existing cross signal configurations such that the vibrator unit is freely received within the chamber formed by the frame and the post, and the panel attached thereto without altering the existing structure.

12. The street crossing signal of claim 8, further comprising an isolation system for retaining the vibrator unit proximal to the indicator window so that upon actuation of the vibrator unit the panel remains substantially stationary.

13. The street crossing signal of claim 12, wherein the isolation system comprises a mounting structure and a plurality of isolation pads positioned between the vibration unit and the mounting structure.

14. The street crossing signal of claim 13, wherein frame projects outwardly from the post .

15. A method of providing a street crossing signal for the visually impaired on an existing street intersection post having a pedestrian control box mounted on the side of the post, the box including a frame which defines a chamber with the post, and a flat plate attached to the frame forming a front wall of the chamber, said method comprising:
  (a) removing said plate;

(b) and replacing the plate with an adaptor including an adapter panel of substantially the same size as said plate and having a vibrating unit mounted on the adapter panel with a portion of the vibrating unit exposed through an aperture in the panel, which when energized will vibrate without vibrating the panel, said replacing step including positioning the vibration unit into said chamber, and mounting the panel to said frame, in the position previously occupied by the plate, without mounting the vibrating unit to the frame, except through said panel.

* * * * *